(12) United States Patent
Voris et al.

(10) Patent No.: US 6,852,328 B1
(45) Date of Patent: Feb. 8, 2005

(54) METHOD AND DEVICE FOR PROTECTION OF WOODEN OBJECTS PROXIMATE SOIL FROM PEST INVASION

(75) Inventors: Peter Van Voris, Richland, WA (US); Dominic A. Cataldo, Kennewick, WA (US); Frederick G. Burton, Stansbury Park, UT (US)

(73) Assignee: Battelle Memorial Institute K1-53, Richland, WA (US)

( * ) Notice: Subject to any disclaimer, the term of this patent is extended or adjusted under 35 U.S.C. 154(b) by 0 days.

(21) Appl. No.: 08/771,467

(22) Filed: Dec. 20, 1996

Related U.S. Application Data

(63) Continuation-in-part of application No. 08/350,432, filed on Dec. 5, 1994, now abandoned, which is a continuation of application No. 08/050,761, filed on Apr. 20, 1993, now abandoned, which is a continuation of application No. 07/402,122, filed on Sep. 1, 1989, now abandoned.

(51) Int. Cl.$^7$ .............................................. A01N 25/32
(52) U.S. Cl. ..................... 424/406; 523/122; 514/124; 514/521; 514/523; 514/531; 514/645; 514/765; 424/405; 424/408; 424/409; 424/411; 424/412; 424/417; 424/419; 424/421; 424/78.09; 424/78.31; 424/DIG. 11
(58) Field of Search ................................ 424/405, 408, 424/409, 411–417, 406, 419, 427, 78.09, 78.31, DIG. 11; 514/124, 63, 521, 523, 765, 645; 523/122, 132

(56) References Cited

U.S. PATENT DOCUMENTS

| | | | |
|---|---|---|---|
| 1,999,458 A | 4/1935 | Hollister | |
| 2,269,626 A | 1/1942 | Henry | |
| 2,899,771 A | 8/1959 | Burris | |
| 2,970,404 A | 2/1961 | Beaufils et al. | |
| 3,111,403 A | 11/1963 | Soper | |
| 3,231,398 A | 1/1966 | Pauli | |
| 3,235,366 A | 2/1966 | Seymour et al. | |
| 3,257,190 A | 6/1966 | Soper | |
| 3,367,065 A | 2/1968 | Cravens | |
| 3,384,993 A | 5/1968 | Kane | |

(List continued on next page.)

FOREIGN PATENT DOCUMENTS

| | | |
|---|---|---|
| AU | A 16980/83 | 7/1983 |
| AU | B-23427/84 | 8/1984 |
| AU | A 48655/90 | 8/1990 |
| AU | A 62329/90 | 3/1991 |
| AU | B-82443/91 | 2/1992 |

(List continued on next page.)

OTHER PUBLICATIONS

Boron as a Preservative Against Internal Decay, Dickinson, Morris, Calver, Distrib. Dev., Mar. 1989, v 89:1, p 9–14.

(List continued on next page.)

Primary Examiner—Neil S. Levy
(74) Attorney, Agent, or Firm—Jenkens & Gilchrist

(57) ABSTRACT

A method and device are disclosed which prevents the decay and deterioration of wooden objects caused by pests by using a controlled release device. This controlled release device utilizes polymers which incorporate pesticides. In the disclosed method, the controlled release device is placed in contact with the wood of the wooden object. The pesticide is gradually released from the device and absorbed into the wood structure. The pesticide absorbed by the wood creates a barrier or an exclusion zone to penetration by inserts. The controlled release device maintains a minimal effective level of pesticide in the barrier or exclusion zone for a predetermined period of time.

35 Claims, 7 Drawing Sheets

U.S. PATENT DOCUMENTS

| | | | | |
|---|---|---|---|---|
| 3,502,458 | A | 3/1970 | Schenk | |
| 3,551,192 | A | 12/1970 | Reinert | |
| 3,592,792 | A | 7/1971 | Newland et al. | |
| 3,608,062 | A | 9/1971 | Alfes et al. | |
| 3,639,583 | A | 2/1972 | Cardarelli et al. | |
| 3,671,548 | A | 6/1972 | Itaya et al. | |
| 3,691,683 | A | 9/1972 | Sterzik | |
| 3,697,253 | A | 10/1972 | MacMurray | |
| 3,705,938 | A | 12/1972 | Hyman et al. | |
| 3,706,161 | A | 12/1972 | Jenson | |
| 3,716,560 | A | 2/1973 | Taya et al. | |
| 3,740,419 | A | 6/1973 | Campbell | |
| 3,741,807 | A | 6/1973 | Home | |
| 3,759,941 | A | 9/1973 | Sampei et al. | |
| 3,835,176 | A | 9/1974 | Matsuo et al. | |
| 3,835,220 | A | 9/1974 | Matsui et al. | |
| 3,846,500 | A | 11/1974 | Kitamura et al. | |
| 3,851,053 | A | 11/1974 | Cardarelli | |
| 3,857,934 | A | 12/1974 | Bernstein et al. | |
| 3,864,114 | A | 2/1975 | Green | |
| 3,864,388 | A | 2/1975 | Kitamura et al. | |
| 3,867,542 | A | 2/1975 | Ueda et al. | |
| 3,876,681 | A | 4/1975 | Okuno et al. | |
| 3,880,643 | A | 4/1975 | Cooke et al. | |
| 3,891,423 | A | 6/1975 | Stanley et al. | |
| 3,899,586 | A | 8/1975 | Okuno et al. | |
| 3,906,089 | A | 9/1975 | Okuno et al. | |
| 3,939,606 | A | 2/1976 | Vandemark et al. | |
| 3,954,814 | A | 5/1976 | Mizutani et al. | |
| 3,966,963 | A | 6/1976 | Okuno et al. | |
| 3,970,703 | A | 7/1976 | Kitamura et al. | |
| 3,981,903 | A | 9/1976 | Hirano et al. | |
| 3,998,868 | A | 12/1976 | Mizutani et al. | |
| 4,003,945 | A | 1/1977 | Kitamura et al. | |
| 4,007,258 | A * | 2/1977 | Cohen et al. | 424/409 |
| 4,021,122 | A | 5/1977 | Krenmayr | |
| 4,037,352 | A | 7/1977 | Hennart et al. | |
| 4,063,919 | A | 12/1977 | Grano, Jr. | |
| 4,065,555 | A | 12/1977 | Potter | |
| 4,066,441 | A | 1/1978 | Lutz et al. | |
| 4,077,795 | A | 3/1978 | Cooke et al. | |
| 4,082,533 | A | 4/1978 | Wittenbrook et al. | |
| 4,101,582 | A | 7/1978 | Lutz et al. | |
| 4,102,991 | A | 7/1978 | Kydonieus | |
| 4,104,374 | A | 8/1978 | Reuther et al. | |
| 4,118,505 | A | 10/1978 | Kitamura et al. | |
| 4,123,250 | A | 10/1978 | Kupelian | |
| 4,160,335 | A | 7/1979 | Von Kohorn et al. | |
| 4,172,904 | A | 10/1979 | Young et al. | |
| 4,176,189 | A | 11/1979 | Itaya et al. | |
| 4,190,680 | A | 2/1980 | Young et al. | |
| 4,193,984 | A | 3/1980 | Kydonieus | |
| 4,198,441 | A | 4/1980 | Young et al. | |
| 4,198,782 | A | 4/1980 | Kydonieus et al. | |
| 4,200,664 | A | 4/1980 | Young et al. | |
| 4,205,096 | A | 5/1980 | Young et al. | |
| 4,212,879 | A | 7/1980 | Ohsumi et al. | |
| 4,229,469 | A | 10/1980 | Mizutani et al. | |
| 4,235,872 | A | 11/1980 | Tocker | |
| 4,237,113 | A | 12/1980 | Cardarelli | |
| 4,237,114 | A | 12/1980 | Cardarelli | |
| 4,243,703 | A | 1/1981 | Palvarini et al. | |
| 4,260,626 | A | 4/1981 | Carr et al. | |
| 4,263,463 | A | 4/1981 | Kitamura et al. | |
| 4,269,626 | A | 5/1981 | Gorke et al. | |
| 4,272,520 | A | 6/1981 | Kydonieus et al. | |
| 4,279,924 | A | 7/1981 | Suzuki et al. | |
| 4,282,207 | A | 8/1981 | Young et al. | |
| 4,282,209 | A | 8/1981 | Tocker | |
| 4,293,504 | A | 10/1981 | Suzuki et al. | |
| 4,320,113 | A | 3/1982 | Kydonieus | |
| 4,327,109 | A | 4/1982 | Mizutani et al. | |
| 4,336,194 | A | 6/1982 | Ohsumi et al. | |
| 4,343,790 | A * | 8/1982 | Pasarela | 424/81 |
| 4,344,250 | A * | 8/1982 | Fahlstrom | 47/57.5 |
| 4,348,218 | A | 9/1982 | Bond, Jr. | |
| 4,350,678 | A | 9/1982 | Palvarini et al. | |
| 4,352,833 | A | 10/1982 | Young et al. | |
| 4,360,376 | A | 11/1982 | Koestler | |
| 4,374,126 | A | 2/1983 | Cardarelli et al. | |
| 4,376,785 | A | 3/1983 | Matsuo et al. | |
| 4,377,675 | A | 3/1983 | Daudt et al. | |
| 4,400,374 | A | 8/1983 | Cardarelli | |
| 4,405,360 | A | 9/1983 | Cardarelli | |
| 4,435,383 | A | 3/1984 | Wysong | |
| 4,457,929 | A | 7/1984 | Kamachi et al. | |
| 4,496,586 | A | 1/1985 | Matsui et al. | |
| 4,500,337 | A | 2/1985 | Young et al. | |
| 4,500,338 | A | 2/1985 | Young et al. | |
| 4,500,339 | A | 2/1985 | Young et al. | |
| 4,503,071 | A | 3/1985 | Hirano et al. | |
| 4,508,568 | A | 4/1985 | Fox | |
| 4,576,801 | A | 3/1986 | Parry et al. | |
| 4,579,085 | A | 4/1986 | McGuire | |
| 4,639,393 | A | 1/1987 | Von Kohorn et al. | |
| RE32,356 | E | 2/1987 | Cardarelli | |
| 4,666,706 | A | 5/1987 | Farquharson et al. | |
| 4,666,767 | A | 5/1987 | Von Kohorn et al. | |
| 4,680,328 | A | 7/1987 | Dohrer et al. | |
| 4,747,902 | A | 5/1988 | Saitoh | |
| 4,767,812 | A | 8/1988 | Chapin et al. | |
| 4,808,454 | A | 2/1989 | Saitoh | |
| 4,818,525 | A | 4/1989 | Kamada et al. | |
| 4,842,860 | A | 6/1989 | Sugiura et al. | |
| 4,886,656 | A | 12/1989 | Obayashi et al. | |
| 4,921,703 | A | 5/1990 | Higuchi et al. | |
| 4,929,497 | A | 5/1990 | Mitchell et al. | |
| 4,971,796 | A | 11/1990 | Sjogren | 424/417 |
| 5,019,998 | A | 5/1991 | Cowen et al. | |
| 5,083,408 | A | 1/1992 | Blom et al. | |
| 5,104,659 | A | 4/1992 | Fishbein et al. | |
| 5,116,414 | A | 5/1992 | Burton et al. | |
| 5,135,744 | A | 8/1992 | Alexander et al. | |
| 5,139,566 | A | 8/1992 | Zimmerman | 71/121 |
| 5,181,952 | A | 1/1993 | Burton et al. | |
| 5,201,925 | A * | 4/1993 | Itzel et al. | 47/58 |
| 5,292,504 | A | 3/1994 | Cardin et al. | |
| 5,296,227 | A | 3/1994 | Norval et al. | |
| 5,317,834 | A * | 6/1994 | Anderson | 424/8.5 |
| 5,439,924 | A | 8/1995 | Mills | |
| 5,449,250 | A | 9/1995 | Burton et al. | |
| 5,492,696 | A * | 2/1996 | Price et al. | 424/417 |
| 5,525,147 | A | 6/1996 | Dunstan et al. | |
| 5,650,163 | A * | 7/1997 | Cannelongo | 424/408 |
| 5,679,364 | A | 10/1997 | Levy | 424/405 |
| 5,698,210 | A | 12/1997 | Levy | 424/406 |
| 5,744,423 | A | 4/1998 | Van Voris et al. | |
| 5,801,194 | A | 9/1998 | Voris et al. | |
| 5,846,553 | A | 12/1998 | Levy | 424/409 |
| 5,856,271 | A | 1/1999 | Cataldo et al. | |
| 5,858,384 | A | 1/1999 | Levy | 424/406 |
| 5,858,386 | A | 1/1999 | Levy | 424/409 |
| 5,860,266 | A | 1/1999 | Martinet et al. | |
| 5,885,602 | A | 3/1999 | Levy | 424/405 |
| 5,885,605 | A | 3/1999 | Levy | 424/405 |
| 5,898,019 | A | 4/1999 | Van Voris et al. | |
| 5,902,596 | A | 5/1999 | Levy | 424/405 |
| 5,902,597 | A | 5/1999 | Iwakawa et al. | |
| 5,925,368 | A | 7/1999 | Voris et al. | |
| 5,939,086 | A | 8/1999 | Levy | 424/405 |
| 5,985,304 | A | 11/1999 | Van Voris et al. | |

| | | | |
|---|---|---|---|
| 6,001,382 A | 12/1999 | Levy | 424/405 |
| 6,060,076 A | 5/2000 | Voris et al. | |
| 6,099,850 A | 8/2000 | Voris et al. | |
| 6,224,957 B1 | 5/2001 | Crook | |
| 6,319,511 B1 | 11/2001 | Van Voris et al. | |
| 6,322,803 B1 | 11/2001 | Van Voris et al. | |
| 6,331,308 B1 | 12/2001 | Van Voris et al. | |
| 6,335,027 B1 | 1/2002 | Levy | 424/409 |
| 6,337,078 B1 | 1/2002 | Levy | 424/406 |
| 6,346,262 B1 | 2/2002 | Levy | 424/408 |
| 6,350,461 B1 | 2/2002 | Levy | 424/409 |
| 6,387,386 B1 | 5/2002 | Levy | 424/408 |
| 6,391,328 B1 | 5/2002 | Levy | 424/406 |
| 6,572,872 B2 | 6/2003 | Van Voris et al. | |
| 2002/0041892 A1 | 4/2002 | Van Voris et al. | |

FOREIGN PATENT DOCUMENTS

| | | |
|---|---|---|
| AU | B-13886/95 | 8/1995 |
| AU | A 52454/96 | 12/1996 |
| CA | 2 070 231 A1 | 12/1992 |
| EP | 0152976 A | 8/1985 |
| EP | 0 286 009 A2 | 10/1988 |
| EP | 0 582 823 A1 | 1/1993 |
| EP | 0 582 823 B1 | 1/1993 |
| EP | 0 594 892 A1 | 5/1994 |
| GB | 2 018 593 A | 10/1979 |
| GB | 2 098 541 A | 11/1982 |
| JP | 52-72802 | 6/1977 |
| JP | 0039601 * | 3/1983 |
| JP | 58 39601 | 3/1983 |
| JP | 5811 3102 | 7/1983 |
| JP | 602 02801 A | 10/1985 |
| JP | 62236937 | 10/1987 |
| JP | 64-58739 A | 3/1989 |
| JP | 6294165 A2 | 10/1994 |
| JP | 8302080 A | 11/1996 |
| SU | 1690654 A1 | 11/1991 |
| WO | WO 84/02447 | 7/1984 |
| WO | WO 90/14004 | 11/1990 |
| WO | WO 92/03927 | 3/1992 |
| WO | WO 95/18532 | 7/1995 |
| WO | WO 95/22902 | 8/1995 |
| WO | WO 96/28973 | 8/1996 ........ A01N/25/28 |
| WO | WO 96/40849 | 12/1996 ....... C10M/111/04 |
| WO | WO 97/47190 | 12/1997 |
| WO | WO 82/21960 | 5/1998 |
| WO | WO 99/41983 | 8/1999 |
| WO | WO 99/42264 | 8/1999 |
| WO | WO 01/08485 A1 | 2/2001 |
| WO | WO 02/43487 A2 | 6/2002 |
| ZA | 86/1133 | 2/1986 |

OTHER PUBLICATIONS

Soil Fumigants are 'Remarkably Effective' in Stopping Decay of Wood Utility Poles, Studies at Oregon State University Suggest, Chemical Week, Sep. 25, 1974, p. 39.

Gelatin Encapsulation of Methylisothiocyanate for Control of Wood–Decay Fungi, Zahora, Corden, Forest Products Journal, vol. 35 (7/8): pp. 64–69, 1985.

Groundline Repair for Wood Poles, EPRI Journal, Apr./May 1986.

Burton, et al., "A Controlled–Release Herbicide Device for Multiple–Year Control of Roots at Waste Burial. Sites," *J. of Controlled Release* (1985), 8 pages.

Chang, et al., "Control of Ant Damage to Polyethylene Tubes Used in Drip Irrigation Systems in Hawaiian Sugarcane Fields," *International. Society of Sugar Cane Technologists* (Feb. 01–11, 1980), pp. 1686–1692.

Chen, et al., "Approaches to the Improvement of Biological Resistance of Wood through Controlled Release Technology," *Proceedings of the 13th Int'l Symposium on Controlled Release of Bioactive Material.s* (Aug. 3–6, 1986), pp. 75–76.

Batelle Technology Transfer Bulletin, "Controlled–Release Chemical.s for Inhibiting Plant Roots," 2 pgs. (12/84).

Cline et al., "Biobarriers used in Shallow Burial. Ground Stabilization," *Nuclear Technology*, vol. 58, pp. 150–153 (1982).

Jury et al., "Behaviour Assessment Model for Trace Organics in Soil: I. Model Description," *J. Environ. Qual.*, vol. 12, No. 4, pp. 558–564, (1983).

Jury et al., "Behaviour Assessment Model for Trace Organics in Soil: III. Application of Screening Model," *J. Environ. Qual.*, vol. 13, No. 4, pp. 573–579, (1984).

Jury et al., "Behaviour Assessment Model for Trace Organics in Soil: IV. Review of Experimental. Evidence," *J. Environ. Qual.*, vol. 13, No. 4, pp. 580–586, (1984).

Roseman et al., "Chapter 18: The Use of Controlled Release Herbicides in Waste Burial. Sites," Controlled Release Delivery Systems Marcel Dekker, NY (1983).

Solie et al., "Simulation of Triflural in Diffusion in the Soil," *Transactions of the ASAE*, pp. 1463–1467 (1984).

Steyaart, "Proceedings, Eighty–Second Annual Meeting of the American Wood–Preservers' Association: Address," *Crossties*, vol. 68, No. 3, pp. 45–46, Mar. 1987.

Streile, "The Effect of Temperature on Pesticide Phase Partitioning, Trasnport, and Volatilization from Soil," *Abstract of the Dissertation*, (1984), 37 pages.

Probst et al., "Fate of Trifluralin in Soils and Plants", J. Agric. Food Chem., vol. 15, No. 4, Jul.–Aug. 1967, pp. 592–599.

Delcourt et al., Chem. Abst., Cytologia, vol. 41, No. 1, Jan. 1976, pp. 75–84.

Lignowski et al., "Trifluralin and Root Growth", Chem. Abst., Plant and Cell Physiology, vol. 76 (1972), pp. 701–708.

Chemical Abstracts, 88, 1978: 154553(5), p. 1177.

Kumar, et al., "The effect . . . treated wood," *J. Timber Dev. . . . India* (1977), 23(3), pp. 9–13.**

Baker and Lonsdale, "Controlled Delivery—an emerging use for membranes", Chemtech, Nov. 1975, pp. 668–674.

Burton et al., "Application of Controlled Release Technology to Uranium Mill Tailings Stabilization", presented at American Nuclear Society Topical Meeting on Waste Management, Feb. 23–26, 1981, Tucson, Arizona, pp. 1009–1021.

Burton et al., "A Controlled–Release Herbicide Device For Multiple–Year Control of Roots at Waste Burial Sites", $10^{th}$ International Symposium on Controlled Release of Bioactive Materials, Jul. 24–27, 1983, San Francisco, California, pp. 305–308.

Burton et al., "The Use of Controlled Release Herbicides in Waste Burial Sites", presented at the Eigth International Controlled Release Symposium, Fort Lauderdale, Florida, Jul. 26–29, 1981.**

PNL–3000–6 Nuclear Waste Management Quarterly Progress Report, Apr. through Jun. 1980. Sep. 1980. Prepared for the U.S. Department of Energy under Contract DE–AC06–76RLO 1830, pp. 22.1 and 22.2, "Application of Long–Term Chemical Biobarriers for Uranium Tailings".**

Eschel et al., Chem. Abstr. vol. 77 (1972), 71309h.**

The Agrochemical.s Handbook, $2^{nd}$ Ed., D. Hartley, ed. The Royal. Society of Chemistry (1987).**

The Pesticide Manual., $8^{th}$ Ed., C. Worthington, Ed., British Crop Protection Council, 1987, pp. 7179–7180.**

Offenlegunsschrift 1929314; Chem. Abstracts vol. 88 entry 75 506 V.**

Morrell, J., Woodpole Conference Proceedings, Mar. 10–11, 1986.**

Hayes, W.C., Extending Woodpole Life: Solving a $5 Billion Dollar a Year Program, Electrical World, p. 41–47, Feb. 1986.

Cooper C., Selecting Fumigants for Treatment of Internal. Decay in Wood, International. Research Group on World Preservation Meeting, May, 1986.**

Shepherd, M., Managing America's Wood Pole Inventory, EPRI Journal., Sep., 1987, vol. 12, No. 6.

Zable, R. et al. The Fungal. Associates, Detection, and Fumigant Control of Decay in Treated Southern Pine Poles, Final. Report EL–27GA for EPRI Research Project 47191, State University of New York, 1982.**

Graham et al. Controlling Biological. Deterioration of Wood with Volatile Chemicals, EPRI Report EL–1480 (Oregon State University), 1980.**

Graham et al. Controlling Biological. Deterioration of Wood with Volatile Chemicals, EPRI Report IL–1480 (Oregon State University), 1977.**

Lucas, G. and Rowell, R. Proceedings from the $13^{th}$ International. Symposium on Controlled Release of Bioactive Materials (Aug. 3–6, 1986), p. 75.**

N.N. Mel'nikov, Chemistry and Technology of Pesticide, Moscow, Khimiya, 1974, pp. 26–30 (translation).

Hughes, J., "Controlled Release Technology Inhibits Root Growth," Controlled Release, p. 15, date unknown 1989.

Van Voris, P., "Long Term Controlled–Releases of Herbicides: Root–Growth–Inhibiting Biobarrier Technology," pp. 1–19, date unknown 188.

Eshel et al., Chem. Abst. vol. 77 (1972), 71309h.

Y. Eshel et al., "Effect of Dinitroanilines on Solanaceous Vegetables and Soil Fungi", *Weed Science*, pp. 243–246, vol. 20, Issue 3, May 1972.

A. Pajak et al., "Morphological and Cytological Effects Brought About By Trifluralin on Pea (*Pisum saativum L.*)", *Biuletyn Warzywniczy*, pp. 451–462, 1979, (abstract provided as first page).

Pajak et al., Chem. Abst., vol. 94 (1981), 133986p.

Chen, G. and Rowell, R., "Proceedings from the $13^{th}$ International Symposium on Controlled Release of Bioactive Materials," Aug. 3–6, 1986, pp. 75–76.

P. Van Voris et al., "Long–Term Controlled–Release of Herbicides Root–Growth Inhibition", Chapter 18 from the ACS (American Chemical Society) Symposium Series, pp. 222–240, 1988.

"Termfilm Termigranuls, The Anti Termite Solution", by Cecil Co., Oct. 18, 1996, 5 pages.

Termite Resistant Sheet for Moisture Permeable Building Material Obtained by Adding Anti–Termite Agent Into Laminated Sheet Obtained by Laminating Nonwoven Fabric or Woven Cloth onto Porous Polyolefin Sheet, 01058739/PN Mar. 6, 1989.

Database WPI Section CH Week 8547 Derwent Publications Lt. London GB Class A97 AN–85–293614 1985.

French Pat. 2,358,831. Chem. Abst. vol. 89, (1978), 15877f. Index Citation.

The Agrochemicals Handbook, $2^{nd}$ Ed., D. Hartley, ed. The Royal. Society of Chemistry (1987). (39 selected pages).

The Pesticide Manual., $8^{th}$ Ed., C. Worthington, Ed., British Crop Protection Council, 1987, pp. 7179–7180. (Table of Contents and 146 selected pages).

Kumar et al., "The Effect . . . Treated Wood," J. Timber Dev. . . . India (1977), 23(3), pp. 9–13.

Offenlegunsschrift 1929314; Chem. Abstracts vol. 88 entry 75 506 V. 1970.

Morrell, J., Woodpole Conference Proceedings, Mar. 10–11, 1986. (Table of Contents and 101 selected pages).

PNL–3000–6/UC–70 Nuclear Waste Management Quarterly Progress Report, Apr. through Jun. 1980. Sep. 1980. Prepared for the U.S. Department of Energy under Contract DE–AC06–76RLO 1830, "Application of Long–term Chemical Biobarriers for Uranium Tailings". By J.F. Cline—Project Manager, pp. 22.1 and 22.2.

Zable, R. et al. The Fungal Associates, Detection, and Fumigant Control of Decay in Treated Southern Pine Poles, Final. Report EL–27GA for EPRI Research Project 47191, State University of New York, 1982. (Table of Contents and 95 selected pages).

Graham et al. "Controlling Biological Deterioration of Wood with Volatile Chemicals", EPRI Report EL–1480 (Oregon State University) 1980. (Table of Contents and 83 selected pages).

Dickinson, Morris and Calver, Boron as a Preservative Against Internal Decay, Distrib. Dev., Mar. 1989, v 89:1, pp. 9–14.

Zahora and Corden, Gelatin Encapsulation of Methyl-isothiocyanate for Control of Wood–Decay Fungi, Forest Products Journal, vol. 35 (7/8): pp. 64–69, 1985.

Groundline Repair for Wood Poles, EPRI Journal, vol. 11, No. 3, Apr./May 1986.

* cited by examiner

METHOD AND DEVICE FOR PROTECTION OF WOODEN OBJECTS PROXIMATE SOIL FROM PEST INVASION

CROSS REFERENCE TO RELATED APPLICATIONS

The present application is a Continuation-In-Part of U.S. patent application, Ser. No. 08/350,432 filed on Dec. 5, 1994 abandoned, which is a continuation of U.S. patent application, Ser. No. 08/050,761 filed Apr. 20, 1993 now abandoned, which is a continuation of U.S. patent application, Ser. No. 07/402,122 filed Sep. 1, 1989, now abandoned.

BACKGROUND OF THE INVENTION

This invention pertains to protection of wooden objects in direct contact with soil from pest invasion and is particularly applicable to protection of wooden utility poles, wooden railroad ties and wooden fence posts.

Preserving wood from decay has been recognized as a problem from ancient times. Noah's wooden ark was preserved with pitch (Genesis 6:14). Roman books on architecture had descriptions "of preserving trees after they are cut, what to plaster or anoint them with, of the remedies against their affirmities, and of allotting them their proper place in the building." (See W. C. Hayes, ed., "*Extending Wood Pole Life: Solving a $5-billion/year Problem*", ELECTRICAL WORLD, 41–47 at 42 (February 1986).

In modern times, the protection of wooden utility poles, railroad ties and fence posts from decay has become a major concern. The decay of such wooden objects has been found to be primarily caused by the action of pests and particularly of fungi, termites, carpenter ants, and other wood invading insects.

The decay caused by fungi is a common and an important source of deterioration of wooden objects by removal or severing of fibers which weakens the wooden object. (See R. A. Zabel et al., *The Fungal Associates, Detection, and Fumigant control of Decay in Treated southern Pine Poles*, Final Report EL-2768 for EPRI Research Project 1471–1, State University of New York 1982). Although decay most frequently occurs within 50 centimeters of the ground line, any part of the pole which has a moisture content of above 20% and is in contact with oxygen can harbor decay-producing fungi. The secondary region of decay is the cross-tie inter-section area. The fungi feed on wood by extending networks of minute, threadlike strands of single cells (hyphae) through the cracks in the wood. The hyphae secrete enzymes that dissolve the cellulose and lining in the wood, transforming them into simple chemicals that the fungi then use as food. In its incipient stages, decay is often invisible to the naked eye, but it is capable of completely destroying large volumes of wood. The termites, carpenter ants and other wood invading insects bore into the wood, thereby destroying its integrity and structural strength. The problem of invasion by pests is exacerbated by the cracking of wood upon drying. As wood dries to below about 30 percent moisture content, it shrinks. Since the moisture level of freshly-cut wood decreases with the distance from the center, as the wood dries, it produces V-shaped cracks, which expose additional surface for penetration by pests. Additionally, any protection of a wooden object which is limited to the outside surface of such object is rendered inoperative once cracks are formed.

The magnitude of the problem of decay of wood is best illustrated by focusing on wooden utility poles. There are about 120 million wooden utility poles in service in the United States, of which 15 to 20 million are currently in need of treatment to remain in service, and 4 to 6 million more become defective each year. A survey by the Electric Power Research Institute ("EPRI") indicated that, on average, it costs $810 to replace an electric distribution pole, and $1690 to replace an electric transmission pole.

The presently accepted commercial approach to protection of new utility poles involves pressure treatment of the outer layers of the lower portions of poles with various organic or inorganic compounds. One widely used preservative is creosote, produced by the destructive distillation of coal. Another organic preservative that has been commonly used to impregnate wooden objects, including utility poles, is pentachlorophenol ("penta"). However, its use in the United States has been severely restricted by the U.S. Environmental Protection Agency. Wooden poles are also impregnated with inorganic compounds, such as chromated copper arsenical (CCA), ammoniacal copper arsenate (ACA) or ammoniacal copper zinc arsenate (ACZA) compounds. A problem with these inorganic wood impregnants, however, is that they leach out and quickly lose their effectiveness in preserving the wood.

A problem common to treatment of wood by impregnation with either organic or inorganic preservatives is that the impregnants reach only the surface layers of the wooden objects. Accordingly, wood cracking exposes untreated areas which are subject to decay.

The pressure impregnation approach provides limited decay protection for a few years up to generally about 15 years. Moreover, the pressure impregnation approach cannot be applied to wooden poles already in place. The decay protection of poles already in place may be extended by periodic inspection and treatment, as necessary, with the fumigants, such as chloropicrin (trichloronitromethane), VAPAM (sodium methyldithiocarbamate) a non-volatile solid which is hydrolyzed to form (methyl isocyanate) or VORLEX, a volatile liquid containing the active ingredient of methyl isocyanate in conjunction with physical strengthening of the deteriorated pole. Such remedial treatment has been shown to arrest fungal activity in Douglas fir poles for up to 10 years. (See R. D. Graham et al., *Controlling Biological Deterioration of Wood with Volatile Chemicals*, EPRI Report EL-1480 (Oregon State University, 1980). The treatment with fumigants generally involves drilling a hole at ground level downward and toward the center of the pole and pouring of the fumigant into the hole. The physical strengthening of the deteriorated pole generally involves placing reinforcing structures, such as metal sheath, concrete poured jackets, or an adjacent supporting pole.

The problem with the current treatment and repair methods is that they are effective for relatively short periods of time and necessitate regular costly manpower-intensive inspections and continual further treatments and repairs. Providing an excess quantity of an impregnant or a fumigant does not solve the problem of the short duration of the protection. The excess of such impregnant of fumigant is rapidly lost to the air and soil decreasing the long-term effectiveness. Moreover, losses of impregnants or fumigants may cause significant environmental problems. Also, additional impregnants and fumigants are subject to decomposition, which renders them ineffective in the long run and not cost effective in the short run. The concentration of active ingredients resulting from a single application of an impregnant or fumigant starts out well above the minimum level necessary for effectiveness, but decreases rapidly with passing time, dropping quickly below the minimum effective level.

Since a long-term solution to pesticide intrusion is desired, the pesticide which is used to control such intrusion can be incorporated into a controlled release device. A "controlled release device" refers to a substance that results in controlled and sustained release of an active chemical from its surface. The device provides a method for the controlled release of the chemical into the surrounding environment. The chemical released into the environment establishes an effective zone of action.

Presently, there are at least three controlled release packaging systems, including microcapsules, coated granules, and chemically-bound fungicides.

While there are a number of reasons for recommending microencapsulation (it is highly versatile, makes use of a variety of manufacturing techniques, and reduces the toxicity of the contained material), it is essentially a short-term system, with lifetimes measured in months rather than years. Additionally, microencapsulation can add significantly to the cost of the fungicide being encapsulated. Furthermore, this process has no use in protecting the other portion of the pole.

Coated granules have a pesticide absorbed onto a matrix such as clay and then coated with cross-linked resins which helps slow the release rate. Clay loses or releases pesticide over a short period of at most a few weeks.

Chemically-bound pesticides are made by chemically binding the pesticide to a polymer, either by being reacting the pesticide with a preformed polymer, or by attaching the pesticide to a monomer and then cross linking to form the polymer. The amount of pesticide chemically bound in a polymer affects the integrity, strength and properties of the polymer. Accordingly, the amount of pesticide that is chemically bound is limited to less than about 10 wt % to maintain polymer integrity.

A Japanese patent J5 8039-601, JA-1983-03 describes an antibacterial agent placed in a hydrophillic polymer and formed into a stick or tablet that is inserted into a hole into the trunk of a tree. The hydrophillic polymer absorbs moisture from the tree and dissolves thereby releasing the antibacterial agent. This controlled release device would be inoperative in non-living dry wood. In fact, it would be inoperative in an environment of unsteady moisture exposure since overexposure to moisture would result in dissolution too quickly and under exposure to moisture would result in insufficient dissolution to release the antibacterial agent.

There is, therefore, a long felt and unsatisfied need for a device, a method and a system of preserving wooden objects in contact with soil for a prolonged period of time, and independent of moisture exposure by preventing decay and deterioration of such objects by pests such as fungi, termites, ants, and other wood invading objects. The need is particularly keen in connection with the prevention of decay and deterioration of wooden utility poles, railroad ties, and fence posts.

SUMMARY OF THE INVENTION

The present invention provides a device, and a method for preventing, for a prolonged period of time, the decay and the deterioration of wooden objects in contact with soil caused by the invasion of pests such as fungi, termites, ants, and other wood invading insects. The device for releasing any of a variety of pesticidal formulations includes a controlled release device. The controlled release device comprises a polymer matrix which can be selected from one of the four following groups: thermoset polymers, thermoplastic polymers, elastomeric polymers, and copolymers thereof, wherein a pesticide has been incorporated at a pre-polymer or pre-crosslinked stage together with a carrier. The resulting device is preferably in the form of a pellet or rod that is insertable into a hole in the wooden object. It can, however, be applied to the outside surface of the object alone, or in conjunction with the internally placed device. The controlled-release device releases the pesticide at a predetermined rate to establish a biochemical barrier and maintain the effective concentration of the pesticide in the wooden object to prevent invasion of pests for a predetermined period of time. For devices releasing the pesticide outward from inside the wooden object, a minimum effective level is maintained throughout the object, thereby eliminating problems associated with cracking of the wood. Furthermore, such devices are capable of preventing environmental and health problems caused by the unduly high concentration of the pesticide at the surface of wooden objects or in the local environment around the object.

In a preferred embodiment, the pesticide and carrier are mixed first then placed into the pre-polymer.

In accordance with one aspect of the present invention, the device releases pesticide at a high rate initially and a lower, steady rate thereafter. This release profile assures that the wooden object becomes protected in a relatively short period of time, and that, subsequent to reaching the minimum effective level, only the amount of pesticide necessary to replace the degraded pesticide is released. This release profile diminishes potential environmental and health problems of the treatment and reduces the cost of the treatment.

In accordance with another aspect of the present invention, the device is applied to the outside surface of the wooden object in the form of a coat containing pesticide which is released in a controlled manner. The coat is applied to the external surface of the wooden object and maintains the minimum effective level of pesticide at the surface of the wood and/or in the surrounding soil.

In accordance with another aspect of this invention, a member which at least partially covers the surface outside is externally applied to the wood object. This member with reservoirs holding the controlled release device provides the minimum effective level of pesticide to protect the wood structure.

In accordance with the further object of the present invention, the device is placed inside the wooden object at about ground level allowing the pesticide to be carried laterally and longitudinally by molecular and gaseous diffusion and longitudinally primarily by the capillary action of the wood structure and moisture.

The present invention, together with the attendant objects and advantages will best be understood with reference to the detailed description below read in conjunction with the accompanying drawings.

DETAILED DESCRIPTION OF THE INVENTION

It has been discovered that the decay and deterioration of wooden objects maintained in soil, can be prevented for a prolonged period of time by a controlled release device which releases a pesticide at a predetermined rate into the wooden object to maintain at least a portion of such object above the pesticide concentration that can be tolerated by pesticides. The devices of the present invention can prevent pest infestation of wooden objects up to the expected lifetime of such objects. For example, the devices of the present invention can prevent pest caused decay and deterioration of wooden utility poles for at least seven (7) years and preferably at least eighteen (18) years.

The process of the present invention for treating wooden objects can be used on any wooden object; however, as a practical matter, it is mostly useful in treating wooden objects which are proximate soil either within soil, in contact with soil, or sufficiently near soil that pests have access to the wooden object(s). The wooden objects for which the present invention is especially useful include: wooden utility poles, wooden railroad ties, wooden bridge parts, such as bridge bracings, wooden fence posts, and the like. As it should be clear to one skilled in the art, the term "wooden objects" is used herein to refer to objects made of the wood, i.e., out of dead tree trunk and branches. The term "wooden objects" is not intended to refer to live trees.

The device of the present invention can be installed in wooden objects which are already in the soil and in those which have not yet been placed in the soil. The present invention is effective in treating both the wooden objects that have been infested by pests and those which have not yet suffered from pest infestation. After the device of the present invention is installed in the wooden object, it releases the pesticide at a controlled rate into the wood. The device's pesticide-release rate is selected to maintain at least a portion of the wooden object at the minimum effective level.

As used in the specification and the appended claims, the term "minimum effective level" is defined to be the pesticide level which can be tolerated by pests. In some applications, a creation of an exclusion zone which pests cannot penetrate is sufficient to protect the entire object. The creation of such a zone is advantageous in that less pesticide is required than if such a level was maintained throughout the whole object. Also, it often is much less expensive to install devices for creation of such zone than for treating the entire object. Finally, the creation of a pest barrier zone is advantageous for ecological and human safety reasons. This is because most of the object does not contain a pesticide.

Figure 1:
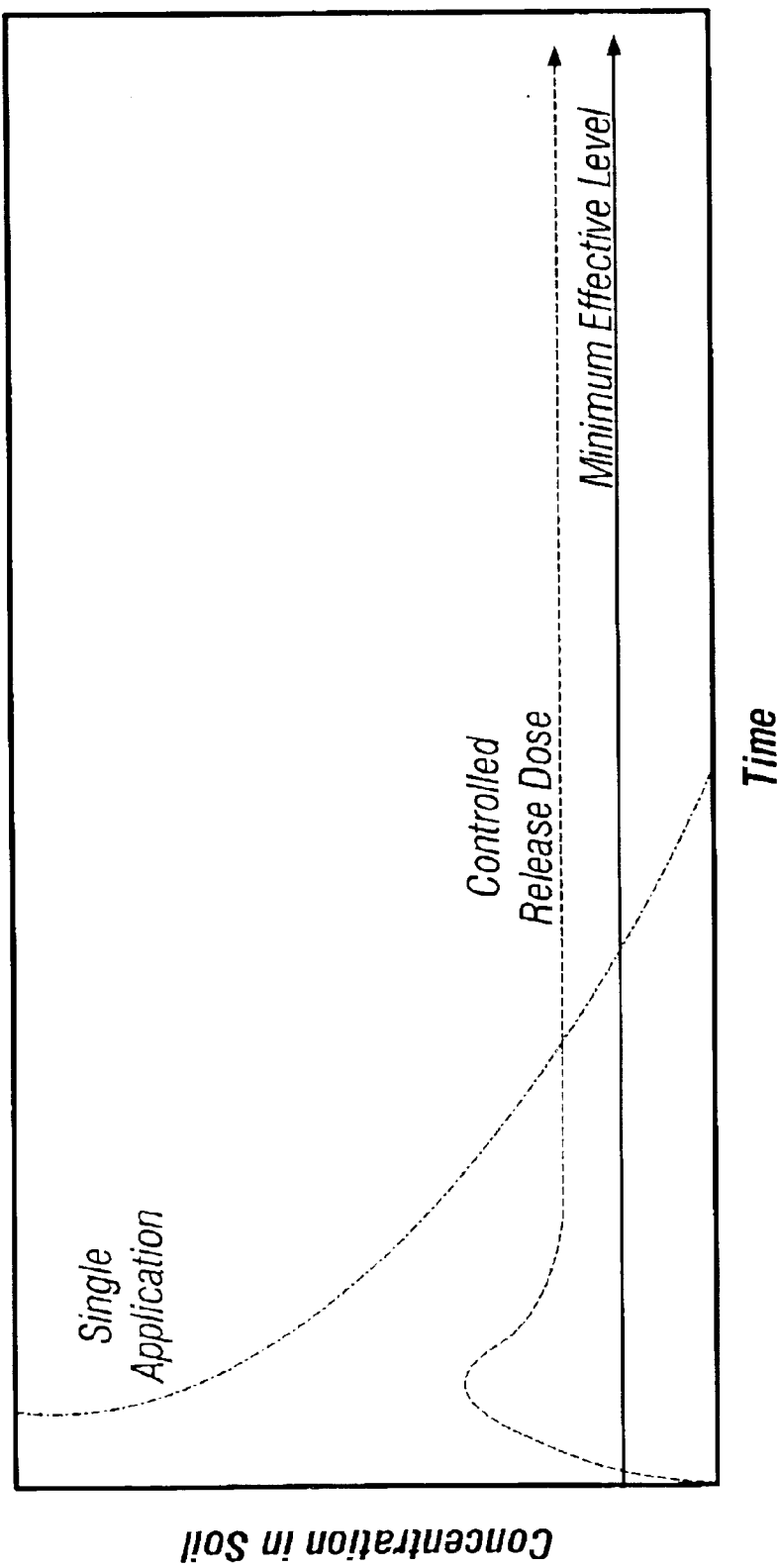
FIG. 1 is a schematic representation of the comparison of concentrations of a pesticide applied in a single dose and by the process and device of the present invention to a wooden object as a function of time.

The controlled release devices of the present invention preferably have a release rate shown in FIG. 1, which is initially rapid so as to bring the pesticide concentration of the zone in the wooden object or the entire object to the desired concentration level as quickly as possible. Thereafter, the release rate is slower, preferably just sufficient to maintain the object or the selected zone of the wooden object above the minimum effective level to prevent pest infestation. The initial high release rate is achieved by allowing the pesticide to release from the matrix prior to inserting the device into or onto the wooden object. The amount of the released pesticide can be varied by the varying temperature and the amount of time for the release prior to inserting the device.

It has been found that hydrophobic polymers serve as effective pesticide release devices because they can act as reservoirs and release regulating mechanisms for the pesticide. They are able to function in this manner because they trap the pesticide within their matrices and matrix acts as a reservoir for the pesticide. Moreover, these polymeric matrices can protect the pesticide from degradation. Thus, the polymeric delivery system is able to maintain an effective dose of the pesticide for a substantial length of time in a zone surrounding the device. A more detailed description of these "controlled release devices" is given in U.S. patent application Ser. No. 06/555,113 filed on Nov. 23, 1983, which is a Continuation-in-Part of Ser. Nos. 06/314,809 and 06/314,810 both filed on Oct. 26, 1981, Ser. No. 07/086,757 filed Aug. 18, 1987, Ser. No. 07/076,080 filed Jul. 10, 1987, and Ser. No. 07/091,918 filed Sep. 1, 1987. The contents of these applications are incorporated herein by reference. Methods for obtaining the release rates are described in patent application Ser. No. 07/303,770 filed on Jan. 30, 1989. Hydrophobicity of the pesticide containing polymer is preferably less than about 13 on either the HLB or solubility parameter scale. More preferred in a hydrophobicity less than about 10 and most preferably less than about 8. Specifically excluded are polymers that are water soluble, and/or have ionic groups (e.g. carboxylic acids, sulfonic acids), and/or have been treated with water to form materials that contain water. However, the present invention includes blends for example polyethylene and POLYOX wherein POLYOX is a water soluble ethylene oxide polymer. However, the active pesticide is contained within the hydrophobic polymer.

The pesticides used in the present invention depend on the anticipated pests which in turn depend on many factors, including the type of wood, the geographical location of the wooden object, and the soil in which the object is maintained. In most cases, the pesticide is selected to eliminate fungi and wood boring insects. The wood boring insects which cause particular problems include carpenter ants and termites (soil born or dry wood). If a single pesticide does not eliminate all of the anticipated pests, the device can incorporate a combination of pesticides, as long as such pesticides are compatible with each other or one another. If the pesticides are not compatible because of different release rates, or, for other reasons, separate devices can be used for treatment in accordance with the present invention. For termites and/or ants, the presently preferred pesticide is a pyrethrin, specifically for example tefluthrin, permethrin, cypermethrin, or combinations thereof. Other preferred pesticides include especially fenoxycarb, and chlorpyrifos, sold under the trademark Chlorophos by Dow Chemical.

For fungi, pesticides include but are not limited to trichloronitromethane under the tradename Chloropicrin, a mixture of methylisothiocyanate and 1-3 dichloropropane under the tradename Vorlex, sodium N-methyl dithiocarbomate under the tradename Vapam, 2,3,5,6-tetracholoro-1,9-benzoquinone under the tradename Chloronil, calcium cyanamide, biphenyl, copper naphthenate, dichlorphen, fentin hydroxide and combinations thereof. Preferred fungicides are biphenyl, dichlorophen, and Chloropicrin, which are water soluble and incorporable into urethane or low density polyethylene. The amount of polymer is preferably about 70 wt % with fungicide in an amount from about 5 wt % to about 30 wt % and a carrier in an amount from about 5 wt % to about 30 wt %.

Polymer selection for the controlled release device depends upon the conditions encountered, either inside the pole, or on its outer surface. The polymer matrices must be able to endure the seasonal variations in temperature and moisture. Moreover, because of their naked exposure to the elements, the matrices used to coat the poles must be able to withstand amplified conditions. The polymer utilized in the coating must meet three requirements. First, it must be bound to the wood pole so that it remains intact during handling. Second, it must provide an adequate diffusion barrier for the pesticide so that the release rate will be compatible with the desired service life. Finally, the selection of the polymer must account for the characteristics of the pesticide.

Polymers capable of withstanding such conditions and providing the desired release rates for the pesticides can be classified into four groups: thermoplastic polymers, thermoset polymers, elastomeric polymer and copolymers thereof. By way of example and not intending to limit the scope of this invention, low density polyethylene, high density polyethylene, vinyl acetate, urethane, polyester, silicone, neoprene, and isoprene polymer and co-polymer can all be used in this invention.

Where synthetic pyrethroids are used, high density polyethylene is the preferred polymer, specifically polyethylene MA778000. More specifically, pyrethroids having both low water solubility and low vapor pressures, the low vapor pressures in the range of 1 nPa to 100 mPa, including tefluthrin (80 mPa), permethrin (45 nPA), lambdacyhalthrin (200 nPa), resmethrin (1.5 nPa), deltamethrin (0.002 mPa), cypermethrin (0.5 nPa), cyphenothrin (0.12 mPa) and cyfluthrin (1 mPa) are preferred in combination with high density polyethylene. Most preferred are permethrin, cyphenothrin, tefluthrin, or combinations thereof because of their combination of efficacy and their release rates from or through a polymer. For more water soluble active chemicals, urethane, specifically Urethane 2200, Hytrel polyesters, and low density polyethylene, specifically Microthene 763 are used. Water soluble active chemicals include diazinon, chlorpyrifos, fenoxycarb, tralomethrin, methyl isothiocyanate and pentachlorophenol.

In addition, it is advantageous to add filler and/or carrier to optimize the loading of the polymer. The inclusion of such a substance allows greater amounts of pesticide to be loaded into the desired polymer, while, at the same time, assisting in the release rate of the polymer. Carbon black is the preferred carrier. More specifically, Vulcan XC-72 is preferred because Vulcan XC-72 has greater adsorption capacity compared to other carbon blacks. For active chemicals that are liquid at room temperature, for example diazinon (pesticide) and copper naphthanate (fungicide), hydroxyapatite is the preferred carrier. For high density polyethylene, the preferred amount of high density polythene is about 70 wt % and low vapor pressure active chemicals in an amount of about 10 wt %, with the carrier in an amount of about 20 wt %. For low density polyethylene, polyester, urethane the preferred amount of plastic is about 65 wt %, and water soluble active chemicals of about 15 wt %, with the amount of carrier about 0 wt % to about 25 wt %. For all combinations, active chemical may range from about 5 wt % to about 30 wt % and carrier from about 0 wt % to about 25 wt %.

When a carrier is added, it has been found that simply adding the carrier to a mix of pesticide and pre-polymer results in poor formability of the controlled release device and permits evaporation of the pesticide. Accordingly, it is preferred to first mix the pesticide into the carrier so that the pesticide is preferably bound either onto the surface of the carrier or into the bulk volume of the carrier or both. The mix of pesticide and carrier is then combined with a polymer. The mix of pesticide and carrier may be combined with a pre-polymer. The bound pesticide is retarded or prevented from evaporation during subsequent forming of the polymer. The pesticide is best mixed with carrier with the pesticide in a liquid form. Some pesticides are in liquid form at room temperature, and others are solid or near solid at room temperature. Accordingly, heating the pesticide may be necessary to insure a liquid form for mixing with the carrier. For the pesticide in solid form with a high melting temperature, for example the fungicide carbendazin, the solid form is preferably a powder or granular form mixed with the carrier. The pesticide may be in the form of a paste and mixed with a carrier.

In a further embodiment, the controlled release device is constructed in two parts, an inner part surrounded by an outer part. The inner part comprises a mix of pesticide and carrier with the outer part a hydrophobic polymer encapsulating the inner part. The outer part may also contain pesticide and carrier that is the same or different compared to the inner part.

The inner part preferably has about 60 wt % pesticide, 30 wt % carrier and 10 wt % polymer, and may range from about 5 wt % to about 70 wt % pesticide, 10 wt % to about 95 wt % carrier and 0 wt % to about 85 wt % polymer.

Forms of the controlled release device include sheets, rods, pellets, and two-part constructions including inner part and outer part rods or pellets, and/or multi-laminate sheets wherein one sheet contains the pesticide or pesticide and carrier and another sheet is added to prevent photodegradation of the pesticide from light exposure.

If the controlled release device is inserted into the wooden object, the pesticide must be loaded into the polymer in sufficient amounts to maintain a "minimal effective level." It is preferred to maintain the concentration in parts by weight of the polymer from about 50 to about 80, the concentration of the pesticide from about 5 to about 30, and the concentration of the carrier from about 5 to about 20. By so loading the polymer, the minimum effective level can be maintained for at least seven (7) years. As the concentration profile shown in FIG. 1, a polymeric controlled release device can maintain a minimal effective level of pesticide for much greater periods of time than single application methods.

The devices of the present invention can have any physical shape. If the device is inserted inside the wooden object, it is desirable to have the device shaped to conform to the cavity. Sheets, sleeves, multiple layers, pellets, dots on geotextile, pots, pot covers, and strips are only a few of the shapes that may embody the present invention.

In some cases, it is desirable to incorporate the device into the wood in a liquid or in a gel form, which may or may not solidify once it is incorporated. For example, a pesticide can be incorporated into a molten polymer which can then be injected in a molten state into a cavity in the wooden object. The polymer then solidifies, creating a solid device which fits tightly in the cavity. Similarly, the pesticide in a molten polymer may be spread on a surface or wooden object and allowed to solidify, creating a device which surrounds a portion of the wooden object as illustrated in FIG. 3.

Figure 4:
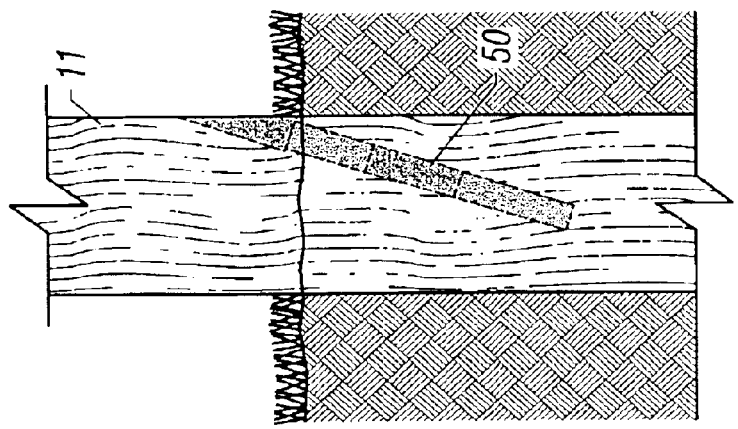
FIG. 4 is a perspective view of the wooden telephone pole of FIG. 3 showing an installed pesticide-releasing device constructed in accordance with the present invention.
Figure 3:
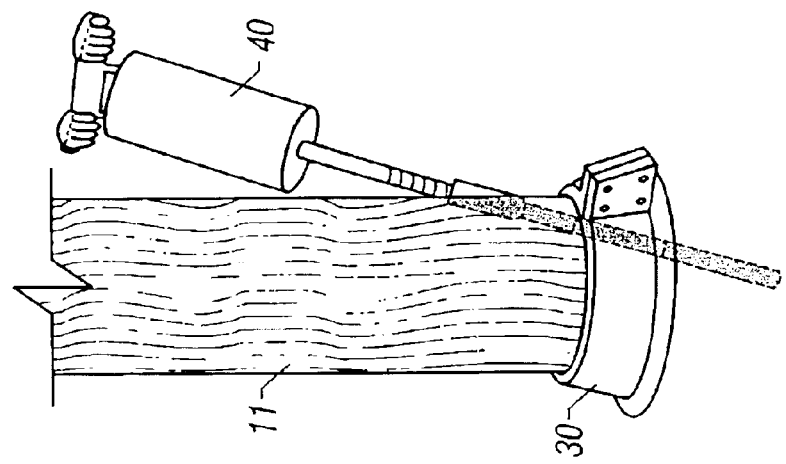
FIG. 3 is a perspective view of a wooden telephone pole being treated by the process of the present invention to install a pesticide-releasing device of the present invention.
Figure 2:
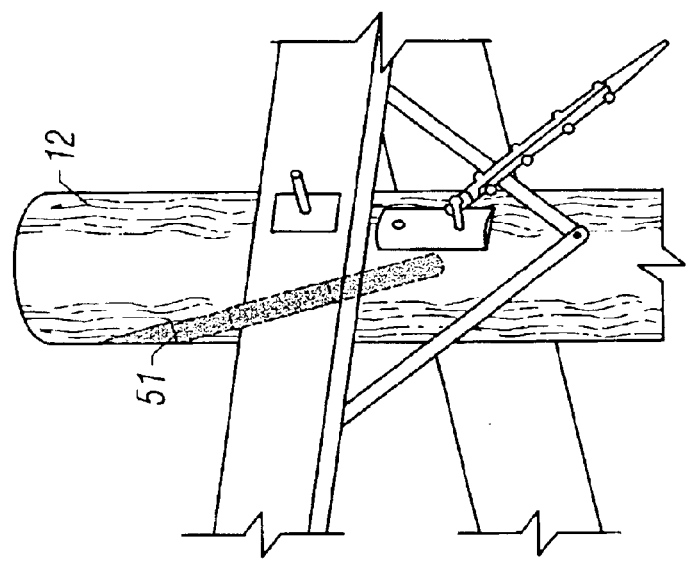
FIG. 2 is a perspective view of a top section of a wooden telephone pole showing the location of the controlled release device constructed in accordance with the present invention.

For utility poles, as illustrated in FIGS. 2–6, it is preferred to insert the device near the center of the pole so that the pesticide is carried outward by diffusion and longitudinally by the capillary action of the wood structure. Once inserted, the opening into the pole must be sealed (not shown in the drawings). Preferably, the seal utilized provides a diffusion barrier for the pesticide. Since the cavity in the wooden objects is often created by drilling a hole therein, the devices of the present invention are often tubular, as generally shown in FIGS. 2–4. The diameter of the tubular device may be any diameter from thread size to several feet, but is preferably from about 0.5 inch to about 2 inches. The length may be any length but is preferably a length that does not extend beyond the wooden object. For a device inserted longitudinally in a portion of a wooden pole to be placed below grade, it is preferred that the length of the device approximately match the distance of the wooden pole extending below grade.

Figure 5:
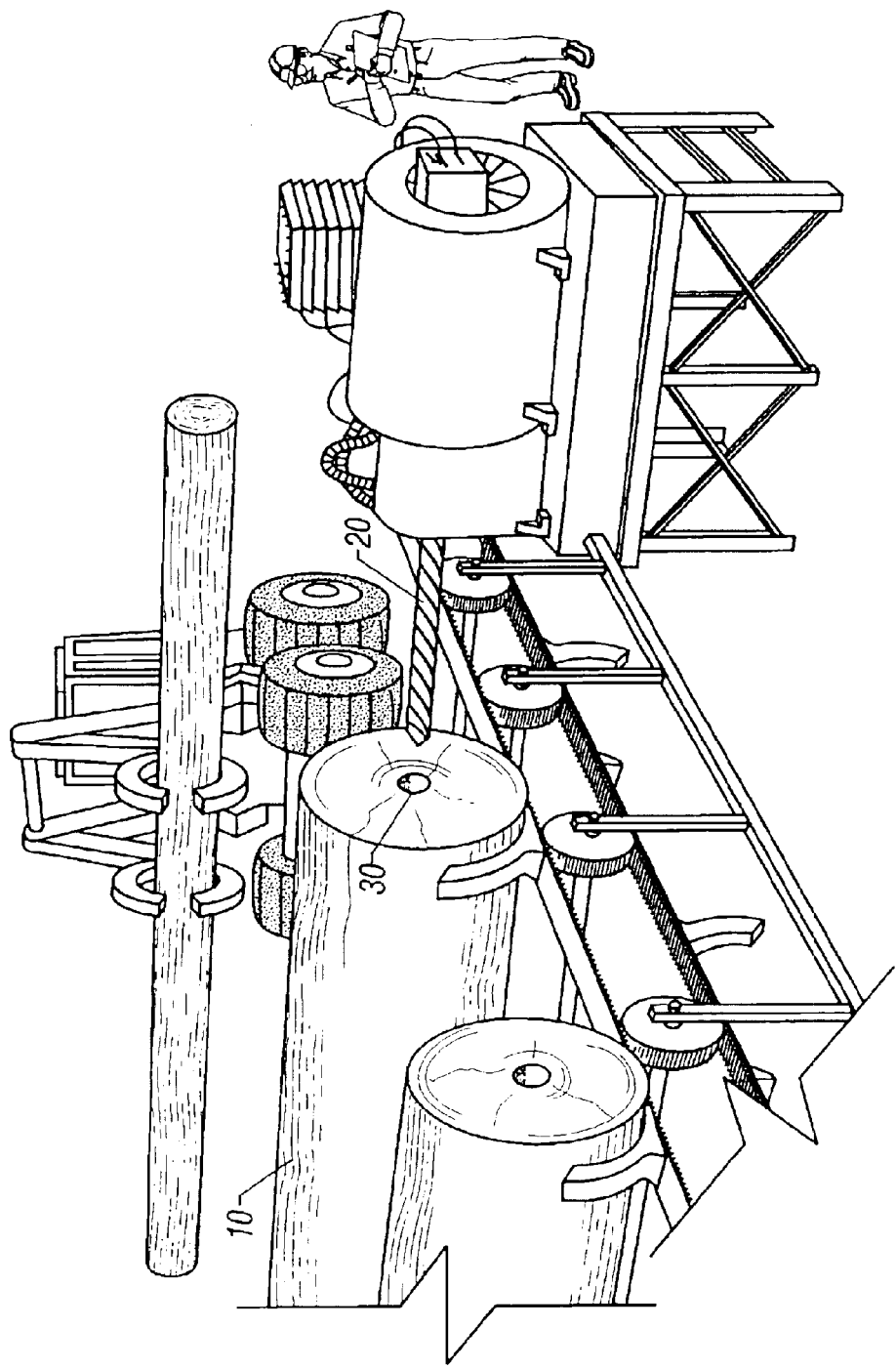
FIG. 5 is a perspective view of drilling operation in the process of installation of the pesticide-releasing device of the present invention into new wooden utility poles.
Figure 6:
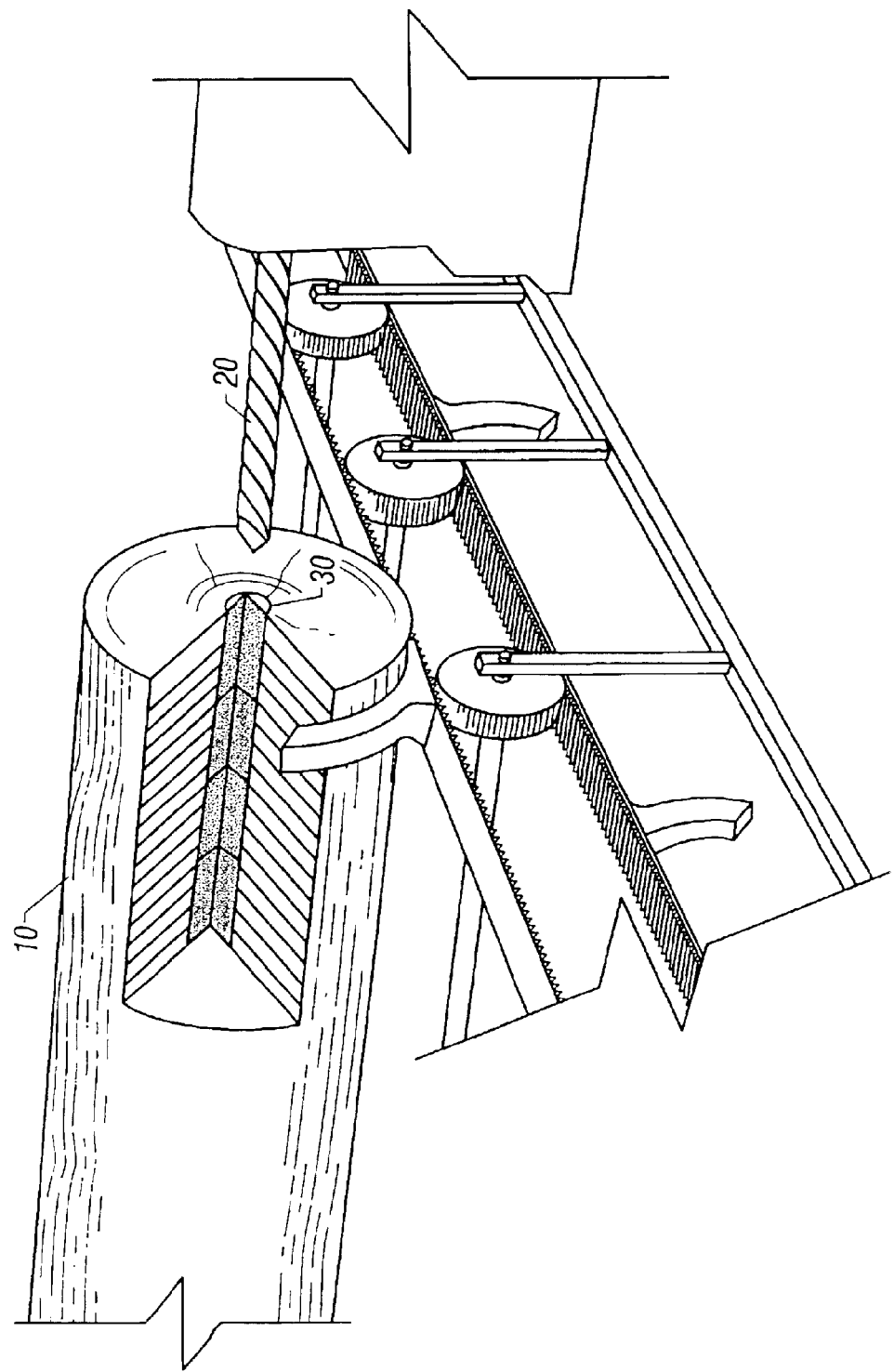
FIG. 6 is a perspective view of the drilling operation of FIG. 5, showing in partial cross-section the bore for the pesticide-releasing device of the present invention.

FIGS. 5 and 6 illustrate the drilling operation of a new utility pole 10. A drill 20 is used to bore a hole 30 in the pole 10 to provide a reservoir for the controlled release device. In distinction, FIG. 3 shows the process of treating an already existing utility pole 11. In this figure, the lower end of the pole 11 is being drilled by a workman using drill 40. A collar 30 is set about the pole 11 to stabilize it as the drill 40 is being pushed downwards into the pole 11. FIG. 4 illustrates the finished pole 11 of FIG. 3 with the controlled release device 50 inserted. FIG. 2 illustrates another embodiment of this invention. It illustrates the controlled release device 51 already inserted near the tope of the utility pole 12.

Figure 7:
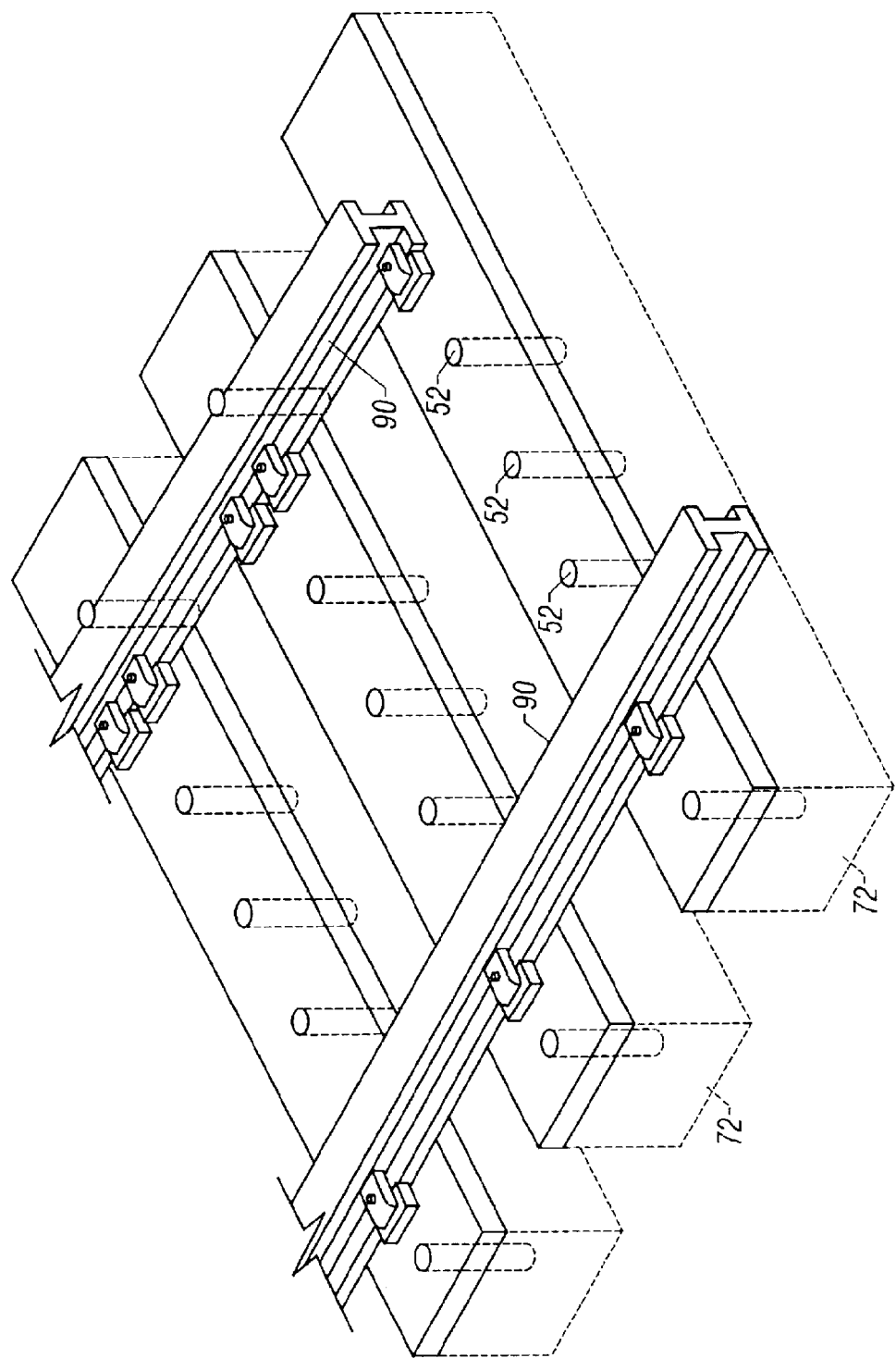
FIG. 7 is a perspective view of the railroad tracks mounted on railroad ties which contain the pesticide-releasing devices constructed and installed in accordance with the present invention.
Figure 8:
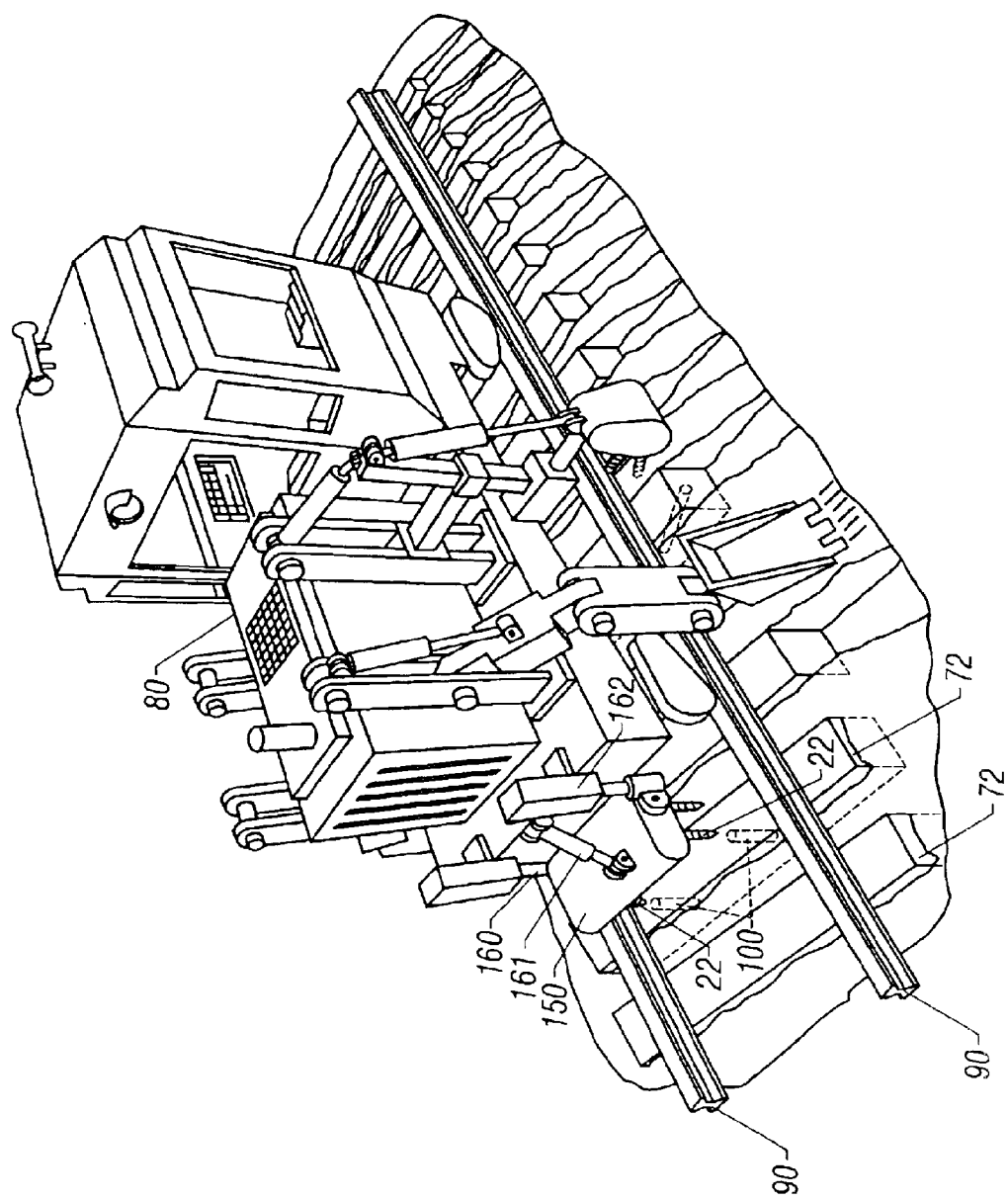
FIG. 8 is a perspective view of a machine for drilling holes in the railroad ties to allow the installation of the pesticide-releasing devices of the present invention.
Figure 9:
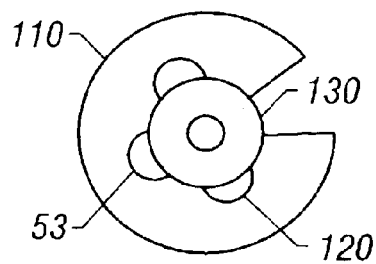
FIG. 9 is a cross-sectional view of a wooden utility pole surrounded by a controlled-release barrier constructed in accordance with an embodiment of the present invention.

For railroad cross-ties 72, it is preferred to insert the controlled release device 52 near the center of the tie 72. FIG. 8 illustrates a preferred mode of application. A mechanism 80, which is capable of movement on rails 90, inserts the controlled release device 52 into cross-ties 72. The mechanism 80 utilizes a plurality of drills 22 to bore holes 100 into the cross-ties 72. Member 150 located at the front of the mechanism 80 houses the drills 22. Pistons 160, 161, 162 raise and lower the member 150 so as to allow mechanism 80 to move to the next cross-tie. FIG. 7 shows the finished product. The controlled release devices 52 have been inserted into cross-ties 72.

In another embodiment of this invention, the polymer is placed in contact with the external surface of the wood object. This embodiment provides immediate protection for the wood. The embodiment maintains a minimum effective level of pesticide at the surface of the wood and, if in contact with the soil, the surrounding soil. Preferably, the concentration in part by weight of the polymer ranges from about 50 to about 80, the concentration of the pesticide from about 50 to about 80, more preferably from about 10 to about 30, and the concentration of the carrier from about 10 to about 20. By so loading the polymer, the minimum effective level can be maintained for at least seven (7) years. However, it should be noted that these concentrations can be varied by the user according to the desired results.

Figure 10:
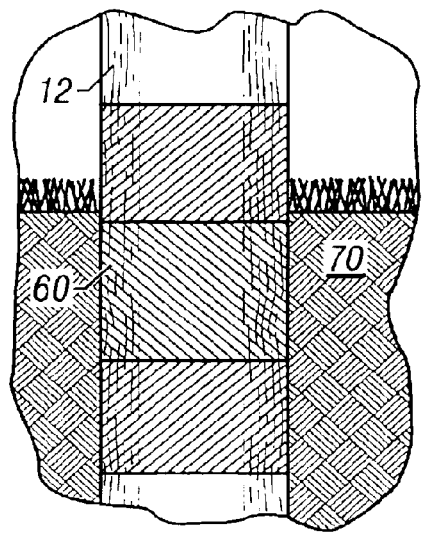
FIG. 10 is a perspective view of the bottom of a wooden utility pole covered with a controlled pesticide release layer constructed in accordance with an embodiment of the present invention.
Figure 11:
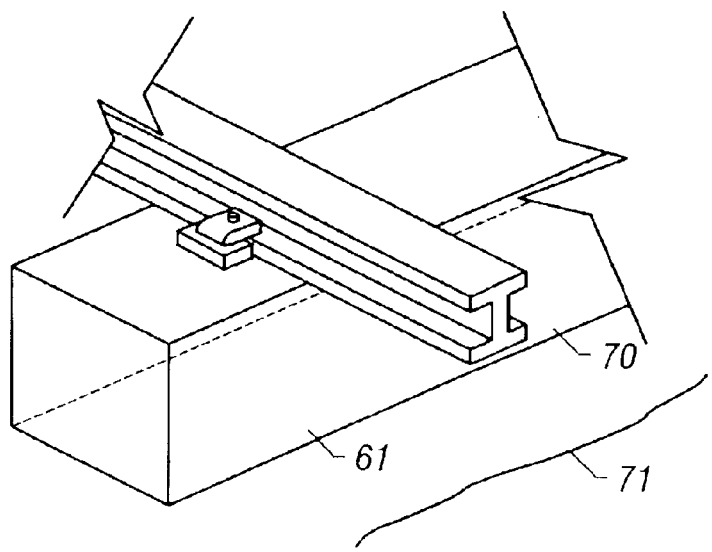
FIG. 11 is a perspective view of a railroad tie whose lower surface is covered with a controlled pesticide release layer constructed in accordance with an embodiment of the present invention.

FIGS. 10 and 11 describe a mode of providing external contact. A coat 60 is applied to pole 12 in FIG. 10. Similarly, a coat 61 is applied to the bottom of a railroad cross-tie 70. These coats 60, 61 are applied in order to protect the wood structures before the pesticide inserted into the core can diffuse through the wood to reach the outer surface of the wooden object. The coat is able to provide an immediate minimum effective level of pesticide. Depending upon the place of application, this minimum effective level of pesticide can also be instituted in the adjacent soil or structure. Both FIGS. 10 and 11 show the wood (pole 12 or cross-tie 70) being in intimate contact with the surface soil 70 or the cross-ties 71.

In another embodiment for providing external contact, a protective outer layer of pesticide can be applied by using a member 110 with reservoirs 120 to hold the controlled release device 53. The member 110 configured as a ring partially covers the wood object 130. The ring 110, as the applied coating, can be placed on the wood object according to user preference. The coating and ring embodiments of this invention have been shown by way of example and do not limit the scope of this invention.

The pesticide permeates the wooden object by several mechanisms. First, if a polar, water soluble, pesticide is used and the wood contains enough moisture, the pesticide is carried by the capillary action of the wood structure. Second, the pesticide having vapor pressure of about 1 mm Hg at 25° C. diffuse relatively quickly through the porous molecular wood structure through gaseous diffusion. Such pesticides diffuse through from the center to the periphery of a telephone pole in about 4 to 6 months. The pesticides having vapor pressure equal to or less than about 1 diffuse more slowly, and those having vapor pressure of less than about 0.1 mm Hg do not effectively diffuse through the wood.

As stated above, the controlled release device may be positioned externally and/or internally in a variety of locations with respect to the wooden structure. If placed above ground level, the pesticide is carried laterally and longitudinally by molecular and gaseous diffusion and longitudinally by the capillary action of the wood structure and moisture. If placed at or about at ground level, a minimum effective level can also be maintained in the soil or surface surrounding the wood structure. It should be noted that devices made out of polymers containing solid polymeric particles need not include carbon black unless protection from UV degradation is desired or unless carbon black is required to modify the release rate.

EXAMPLE 1

The following controlled release devices were made and tested to obtain their release rates (Table 1). The devices were made as follows. All devices, except for those employing S-113 urethane, were injection molded into a thin sheet about ⅛ inch thick. The device employing S-113 urethane was case, a method typically used for thermoset polymers. All thermoplastics were formulated using sufficient amount of carbon black to carry pesticides. All thermoplastic polymers were formulated with 10 percent pesticide, 3 or 7 percent carbon black to absorb liquid pesticide and 87 to 83 percent by weight of polymer. Specifically, devices made from thermoplastic polymers and deltamethrin and lambda-cyhalothrin contained 3 percent of carbon black. The devices made from the remaining pesticides and thermoplastic polymers contained 7 percent of carbon black.

The devices made from S-113 urethane (a thermoset polymer) were made from a polymer mix containing 60% S-113, 40% castor oil, and 5% of TIPA catalyst by weight. The polymer mix comprised 90% of the total weight of the device. The pesticide, deltamethrin, comprised the remaining 10% of the device. No carbon black was used in this device. The polymer/pesticide mixture was cast, using a spin caster into a ⅛ inch thick sheet and heated at about 60° C. for about 40 to 60 minutes to cure the cast sheet.

One inch squares were then cut from the thin sheets that were injection molded or cast, and the squares were tested for release rates as shown in Table 1.

TABLE 1

Release Rates for Pesticide/Polymer Combinations

| Pesticide | Polymer | Release Rate |
|---|---|---|
| Deltamethrin | S-113 urethane | 25.2 µg/cm2/day |
|  | Aromatic 80A | 16.8 µg/cm2/day |
|  | pellethane 2102-80A | 8.8 µg/cm2/day |
|  | pellethane 2102-55D | 8.0 µg/cm2/day |
|  | Alipmtic PS-49-100 | 7.2 µg/cm2/day |
| Cypermethrin | polyurethane 3100 | 0.4 µg/cm2/day |
|  | polyurethane 2200 | 0.7 µg/cm2/day |
|  | EVA 763 | 27.3 µg/cm2/day |
|  | Polyethylene MA78000 | 4.6 µg/cm2/day |
| Lambdacyhalothrin | polyurethane 3100 | 0.7 µg/cm2/day |
|  | polyurethane 2200 | 2.0 µg/cm2/day |
|  | EVA 763 | 20.6 µg/cm2/day |
|  | Polyethylene MA78000 | 5.2 µg/cm2/day |
| Tefluthrin | polyurethane 3100 | 6.4 µg/cm2/day |
|  | polyurethane 2200 | 25.0 µg/cm2/day |
|  | EVA 763 | 40.4 µg/cm2/day |
|  | Polyethylene MA78000 | 27.0 µg/cm2/day |
| Permethrin | polyurethane 3100 | 1.4 µg/cm2/day |
|  | polyurethane 2200 | 1.3 µg/cm2/day |
|  | EVA 763 | 28.5 µg/cm2/day |
|  | Polyethylene MA78000 | 4.0 µg/cm2/day |
| Dichlorophen | Polyethylene MA78000 | 6.2 µg/cm2/day |

EXAMPLE 2

Controlled release devices in the form of sheets are made having 10% wt % pesticide, 10 wt % carrier and 80 wt % high density polyethylene (MA 778000). Longevity as a function of sheet thickness is shown in Table 2.

TABLE 2

Release Rate and Longevity as a Function of Sheet Thickness and Temperature

| Pesticide | Sheet Thickness (mil) | Release Rate (µg/cm$^2$/day) @ 23° C. | Longevity (years) @ 23° C. | Longevity (years) @ 35° C. |
|---|---|---|---|---|
| Permethrin | 60 | 1.5 | 8.6 | 3.2 |
|  | 120 |  | 17 | 6.5 |
|  | 240 |  | 35 | 13 |
| Tefluthrin | 60 | 1.3 | 9.1 | 3.1 |
|  | 120 |  | 18.2 | 5.9 |
|  | 240 |  | 39 | 10.4 |
| Diazinon | 60 | 11.7 | 1.1 | 0.6 |
|  | 120 |  | 2.3 | 1.3 |
|  | 240 |  | 4.8 | 2.7 |
| Biphenyl | 60 | 3.5 | 2.5 | 2.1 |
|  | 120 |  | 5.1 | 4.4 |
|  | 240 |  | 11.2 | 9.1 |
| Dichlorophen | 60 | 6.2 | 1.6 | 1.4 |
|  | 120 |  | 3.3 | 3.0 |
|  | 240 |  | 6.8 | 6.4 |

Release rates are substantially decreased compared to those in Tables 1 and 2 by an additional layer, for example metallized polyethylene terephthalate (Mylar) or poly (vinylidene chloride) (Saran) that is added to prevent photodegradation.

EXAMPLE 3

A device having an inner part surrounded by or encapsulated by an outer part is constructed having an overall mass of about 100 g. The inner part contains 60 wt % pesticide and 40 wt % carrier. The outer part is high density polyethylene of a thickness of 120 mil. Release rates are shown in Table 3.

TABLE 3

Release Rate for Encapsulated Two-Part Construction

| Pesticide | Release Rate (µg/cm$^2$/day) @ 23° C. | Longevity (years) @ 23° C. | Longevity (years) @ 35° C. |
|---|---|---|---|
| Permethrin | 16 | 68 | 38 |
| Tefluthrin | 31 | 35 | 18 |
| Diazinon | 28 | 39 | 24 |
| Biphenyl | 35 | 31 | 23 |
| Dichlorophen | 24 | 56 | 28 |

EXAMPLE 4

A pellet is made having a mass of about 100 g and a surface area of about 150 cm$^2$. The polymer is 70 wt % high density polyethylene, with 20 wt % pesticide and 10 wt % carrier. Release rates are shown in Table 4. Comparing Table 4 to Table 3, it is evident that the encapsulated two-part construction provides longer life than the pellet.

TABLE 4

Release Rates From Pellet

| Pesticide | Release Rate (µg/cm$^2$/day) @ 23° C. | Longevity (years) @ 23° C. | Longevity (years) @ 35° C. |
|---|---|---|---|
| Permethrin | 12 | 30 | 14 |
| Tefluthrin | 11 | 33 | 16 |

TABLE 4-continued

Release Rates From Pellet

| Pesticide | Release Rate ($\mu$g/cm$^2$/day) @ 23° C. | Longevity (years) @ 23° C. | Longevity (years) @ 35° C. |
| --- | --- | --- | --- |
| Diazinon | 45 | 8.1 | 5.1 |
| Biphenyl | 16 | 22 | 11 |
| Dichlorophen | 11 | 33 | 16 |

Closure

It should be apparent that a wide range of changes and modifications can be made to the embodiments described above. It is, therefore, intended that the foregoing description be regarded as illustrative rather than limiting, and that it be understood that it is the following claims, including all equivalents, which are intended to define this invention.

What is claimed is:

1. A method of making a matrix for controlled release of at least one pesticide useful for retarding or preventing decay or deterioration of a wooden object by pests, the method comprising the steps of:

(a) forming a mixture comprising at least one liquid pesticide, a plurality of carrier particles, and a hydrophobic thermoplastic polymer to bind a sufficient amount of the pesticide to the carrier particles to form pesticide-containing carrier particles so as to reduce the release rate of the pesticide from the controlled release matrix to the range from 0.4 $\mu$g/cm$^2$/day to 40.4 $\mu$g/cm$^2$/day, the at least one liquid pesticide is selected from the group consisting of liquid pyrethrin, tefluthrin, permethrin, cypermethrin, fenoxycarb, chlorpyrifos, lambdacyhalothrin, resmethrin, deltamethrin, cyphenothrin, cyfluthrin, and combinations thereof; and (b) forming the pesticide-containing carrier particles and the polymer into a controlled release matrix having pesticide-containing carrier particles dispersed throughout the polymer.

2. The method as recited in claim 1, wherein the at least one pesticide is formed by heating a solid pesticide to convert the solid pesticide into the at least one liquid pesticide prior to said binding step.

3. The method as recited in claim 1, wherein said hydrophobic polymer has a hydrophobicity of less than about 13 on either the hydrophilic lipophilic balance or solubility parameter scale.

4. The method as recited in claim 1, wherein said forming comprises enveloping said mixture as an inner part within a second hydrophobic polymer.

5. The method claimed in claim 1, wherein the pesticide is lambdacyhalothrin.

6. The method claimed in claim 1, further comprising the step of shaping the mixture of the pesticide-containing carrier particles and the polymer into a multi-laminate sheet.

7. The method as recited in claim 1, wherein said hydrophobic thermoplastic polymer is selected from the group consisting of low density polyethylene, high density polyethylene, ethylene vinyl acetate copolymer, polyester, silicone, neoprene, isoprene polymer and copolymer, and combinations thereof.

8. The method as recited in claim 1, wherein the at least one said pesticide has a vapor pressure in the range from 1 nPa to 100 mPa.

9. The method of claim 1, wherein the release rate of the pesticide from the controlled release matrix is reduced so as to retard or prevent decay or deterioration of the wooden object by pests for a period of at least about 7 years.

10. The method as recited in claim 1, wherein the polymer is low density polyethylene.

11. The method as recited in claim 1, wherein said pesticide is water soluble.

12. The method claimed in claim 1 wherein the forming step is performed by injection molding.

13. The method claimed in claim 1 wherein the at least one pesticide further includes a pesticide for eliminating wood boring insects.

14. The method claimed in claim 1 wherein the matrix is formed into a pellet.

15. The method claimed in claim 1 wherein the matrix is formed into a sheet.

16. The method claimed in claim 1 wherein the matrix is formed into strips.

17. The method claimed in claim 1 wherein said carrier particles comprise from about 3 to about 30 weight percent of said matrix and said polymer comprises from about 40 weight percent to about 92 weight percent of said matrix.

18. The method of claim 1 wherein said hydrophobic polymer has a hydrophobicity of less than about 10 on either the hydrophilic lipophilic balance or solubility parameter scale.

19. The method of claim 1 wherein said hydrophobic polymer has a hydrophobicity of less than about 8 on either the hydrophilic lipophilic balance or solubility parameter scale.

20. The method of claim 1 wherein the carrier particles comprise carbon black.

21. The method of claim 1 wherein the carrier particles comprise hydroxyapatite.

22. The method claimed in claim 15, wherein the sheet has a thickness in the range from about 60 mil to about 120 mil.

23. The method claimed in claim 1, wherein said at least one pesticide comprises from about 5 to about 30 weight percent of the matrix.

24. A method of making a device for controlled release of at least one pesticide useful for retarding or preventing decay or deterioration of a wooden object by pests, said method comprising the steps of:

(a) binding at least one liquid pesticide to carrier particles to produce pesticide-containing carrier particles; then (b) combining said pesticide-containing carrier particles with a thermoplastic hydrophobic polymer to produce said device, wherein the amount of pesticide bound to the carrier particles is sufficient so as to achieve a release rate of the pesticide from said device in the range from 0.4 $\mu$g/cm$^2$/day to 40.4 $\mu$g/cm$^2$/day.

25. The method as recited in claim 24, wherein the polymer is low density polyethylene.

26. The method as recited in claim 24, wherein the at least one pesticide is an insecticide.

27. The method as recited in claim 24, wherein the pesticide is selected from the group consisting of pyrethrin, tefluthrin, permethrin, cypermethrin, fenoxycarb, chlorpyrifos, lambdacyhalothrin, resmethrin, deltamethrin, cyphenothrin, cyfluthrin, and combinations thereof.

28. The method as recited in claim 24, wherein the pesticide is lambdacyhalothrin.

29. The method as recited in claim 24, wherein the release rate of the pesticide from the matrix is between about 0.7 $\mu$g/cm$^2$/day to about 20.6 $\mu$g/cm$^2$/day.

30. The method as recited in claim 24, wherein the device is in the form of a rod, sheet, sleeve, strip, or pellet.

31. The method claimed in claim 24, further comprising the step of shaping the device into a sheet having at least one additional layer.

32. The method claimed in claim 31, wherein the at least one additional layer is selected from the group consisting of polyethylene terephthalate, polyvinylidene chloride, and combinations thereof.

33. The method claimed in claim 24, further comprising the step of shaping the device into a multi-laminate sheet.

34. The method claimed in claim 24 further comprising the step of shaping the device into a pellet.

35. The method as recited in claim 24, wherein the polymer is selected from the group consisting of low density polyethylene, high density polyethylene, ethylene vinyl acetate copolymer, urethane, polyester, silicone, neoprene, isoprene polymer and copolymer, and combinations thereof.

* * * * *

UNITED STATES PATENT AND TRADEMARK OFFICE
CERTIFICATE OF CORRECTION

PATENT NO. : 6,852,328 B1
DATED : February 8, 2005
INVENTOR(S) : Peter Van Voris et al.

It is certified that error appears in the above-identified patent and that said Letters Patent is hereby corrected as shown below:

Title page,
Item [63], Related U.S. Application Data, insert -- Continuation-in-part of application No. 08/484,967, filed on June 7, 1995, now U.S. Patent No. 5,925,368, which issued July 20, 1999, which is a --; before the first word;
Item [56], References Cited, U.S. PATENT DOCUMENTS, delete "Home" and insert -- Horne --;
FOREIGN PATENT DOCUMENTS, delete
"WO    82/21960" and insert -- WO    98/21960 --.

Signed and Sealed this

Fourth Day of April, 2006

JON W. DUDAS
*Director of the United States Patent and Trademark Office*